United States Patent [19]
Fulcher et al.

[11] Patent Number: 5,502,656
[45] Date of Patent: Mar. 26, 1996

[54] DATA LOGGER HAVING A RAM THAT ACCEPTS ELECTRO-MAGNETICALLY A SENSOR TABLE AND A SAMPLE TABLE

[75] Inventors: Malcolm Fulcher; Trevor Storeton-West, both of London, Great Britain

[73] Assignee: The Minister of Agriculture Fisheries and Food in Her Britannic Majesty's Government of the United Kingdom of Great Britain and Northern Ireland, London, England

[21] Appl. No.: 318,810

[22] PCT Filed: Apr. 21, 1993

[86] PCT No.: PCT/GB93/00827

§ 371 Date: Oct. 19, 1994

§ 102(e) Date: Oct. 19, 1994

[87] PCT Pub. No.: WO93/22713

PCT Pub. Date: Nov. 11, 1993

[30] Foreign Application Priority Data

Apr. 30, 1992 [GB] United Kingdom ............... 9209394

[51] Int. Cl.6 .................................................. G01B 21/00
[52] U.S. Cl. ........................................ 364/550; 364/178
[58] Field of Search ............................... 364/550, 554, 364/557, 559, 558, 565, 567, 569, 571.01–571.05, 556, 571.07, 178, 179

[56] References Cited

U.S. PATENT DOCUMENTS

| | | | |
|---|---|---|---|
| 4,969,112 | 11/1990 | Castle | 364/567 |
| 4,987,578 | 1/1991 | Yoshinaka et al. | 377/25 |
| 4,996,655 | 2/1991 | Chadwick et al. | 364/550 |
| 5,299,141 | 3/1994 | Hungerford et al. | 364/516 |

FOREIGN PATENT DOCUMENTS

| | | |
|---|---|---|
| 2153171 | 8/1985 | United Kingdom . |
| 2218237 | 11/1989 | United Kingdom . |
| WO9003070 | 3/1990 | WIPO . |

*Primary Examiner*—James P. Trammell
*Attorney, Agent, or Firm*—Nixon & Vanderhye

[57] ABSTRACT

A data logger includes a housing containing at least one sensor; programmable controller including a pre-programmed Erasable Programmable Read Only Memory (EPROM) containing control instructions and sensor drivers for all sensors; a Random Access Memory (RAM) providing data storage for storing data from each sensor; a power supply; and electromagnetic transfer device for accessing the logger and recovering data from the data storage from external to the casing; the RAM being adapted to accept, from external to the housing and via the electro-magnetic transfer device, instructions on the sensor drivers to evoke a desired sample regime; the logger also including a power up coil is provided within the housing to enable power from the external to the housing to be supplied during programming and during recovery of data.

12 Claims, 6 Drawing Sheets

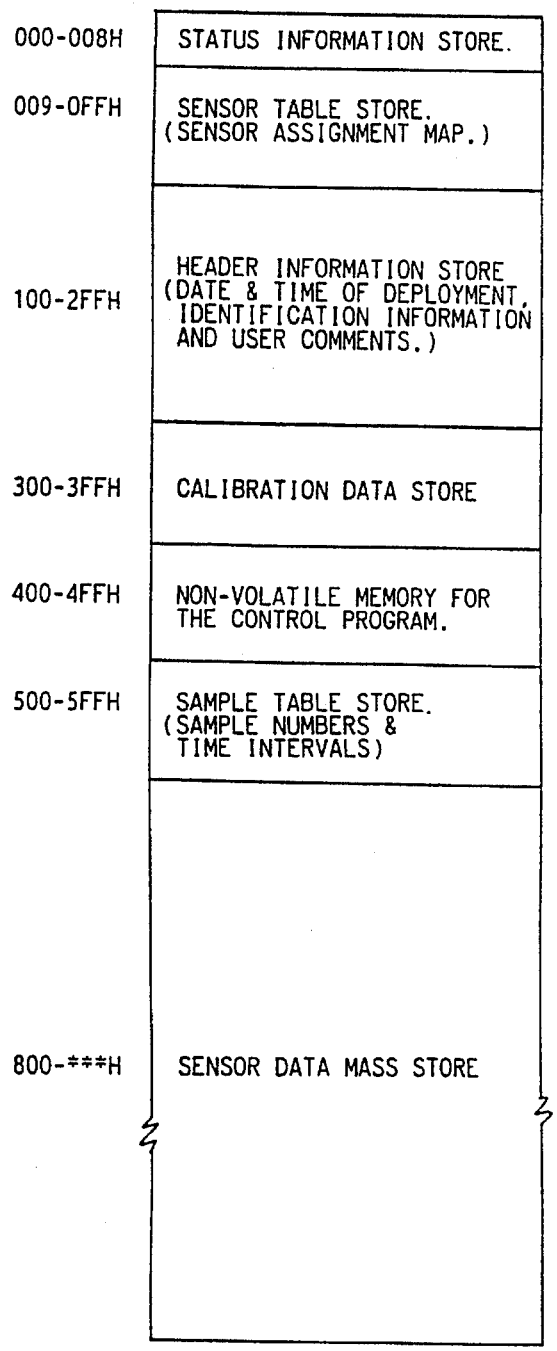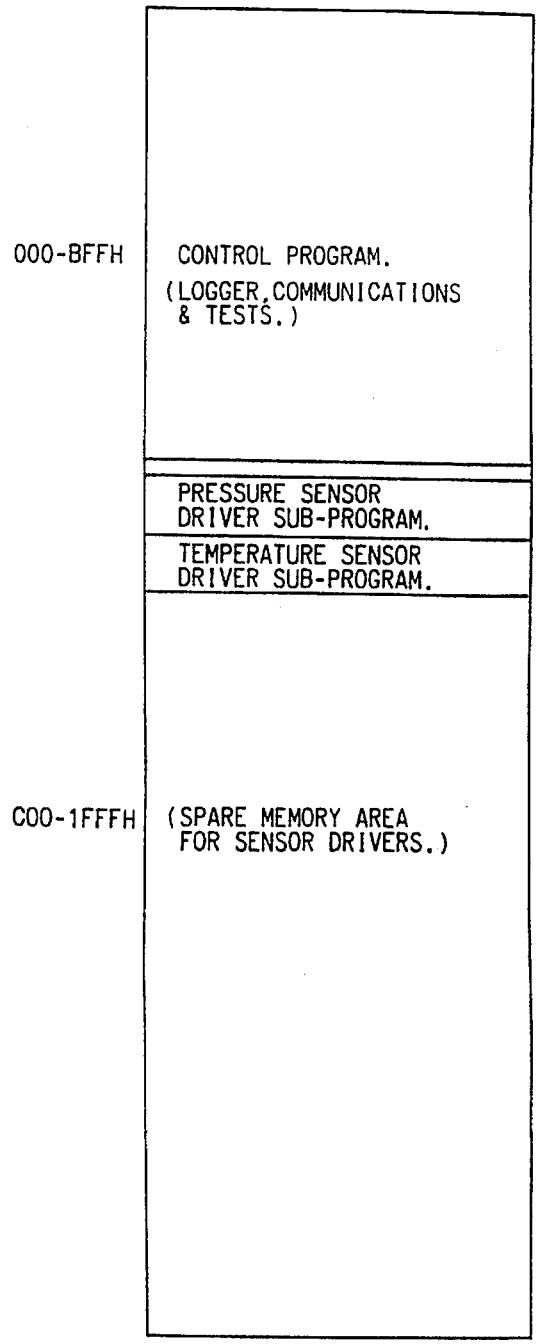
FIG. 7A
RAM MEMORY MAP
FIG. 7B
EPROM MEMORY MAP

DATA LOGGER HAVING A RAM THAT ACCEPTS ELECTRO-MAGNETICALLY A SENSOR TABLE AND A SAMPLE TABLE

This application is a 371 of PCT/GB 93/00827 filed Apr. 21, 1993 having a RAM that accepts electromagnectically a sensor table and a sample table.

BACKGROUND OF THE INVENTION

1. Field of the Invention

The present invention relates to data loggers, particularly, though not exclusively such tags for use on fish and other marine life.

2. Discussion of Prior Art

In order to develop conservationist fishing strategies fish stock management requires information on fish habits and their environment. For this many and varied data are required. Whilst it is possible to track fish shoals or individual fish fitted with suitable transmitters, monitoring positions and aspects of environment at the same time, there are clear difficulties involved in this. To do such monitoring in the open seas requires the expense of a ship. The cost of this is so high that it is usually only possible to afford it for a few days at a time. While tracking fish in this way there is every possibility that contact with the monitored fish will be lost. Thus, even if a continuous watch can be maintained on a fish the duration of the watch can only be a small interval in the seasonal or life cycle of the species under observation.

There is much concern about the depletion of fish stocks. A prime requirement in preventing and reversing the depletion trend, whilst maintaining reasonable fishing hauls, is a knowledge of the behaviour of fish, which would enable conservationist fishing strategies to be developed.

SUMMARY OF THE INVENTION

According to the present invention a data logger includes a housing containing; at least one sensor; programmable control means; a Random Access Memory (RAM) providing data storage means for storing 2 data from the or each sensor; power means; and electro-magnetic transfer means for accessing the logger and for recovering data from the data storage means from external to the casing; characterised in that;

the programmable control means includes a pre-programmed Erasable Programmable Read Only Memory (PROM) containing control instructions and sensor drivers for all sensors;

the RAM is adapted to accept, from external to the housing and via the electro-magnetic transfer means, instructions on the sensor drivers to evoke a desired sampling regime; and a power up coil is provided within the housing to enable power from external to the housing to be supplied during programming and during recovery of data.

The control instructions in the EPROM preferably include an operating programme, a communications program and a test procedure program.

The housing will usually be waterproof, and will of necessity be waterproof when the logger is to be attached to a fish.

The power means will usually be in the form of electric cells and preferably will include a standby cell.

The electro-magnetic transfer means will usually be optical, preferably using light in the infrared region.

The logger will usually be designed to protect stored data by switching to a disabled state automatically once it has completed a sample table, when the mass date store is full, or when it detects that the power supply is low.

A clinical thermometer wherein a temperature responsive portion, a battery and data storage means are contained within a casing, the data storage means acting to store measurements taken at predetermined intervals and being accessible from external to the casing for transfer of data, is described in U.S. Pat. No. 4,987,579. One means of transferring data uses optical means. The predetermined intervals must be set before build of the instrument, and the instrument is designed for use over a short time scale—for example of the order of a day.

The present logger is intended for use over a period of years. The arrangement is such that a logger will usually contain a plurality of different sensors and operating means for actuating each sensor and for recording readings therefrom. However the actual operating program is not set during build, but is only entered prior to use and can be adjusted according to conditions and requirements at the time of commencement of use. Thus, for example, certain sensors may not be used, or only used for short periods during the life of the logger, or used only at long intervals.

Considering the case where a logger is attached to a fish the operating program will be based on factors such as the type of fish, the area which the fish is thought to inhabit, and so on. The fish with logger attached is released and if and when the logger is recovered (for example, by being returned by a fisherman who has caught the fish) the information stored therein can be recovered. The method of programming the logger and of recovering information therefrom does not rely on the logger's internal power supply, thus reducing the danger of losing information as a result of low logger internal power.

It will be realised that the expense of the loggers, and the danger of losing information therefrom, must be kept to a minimum as not all will be recovered to provide information. It is estimated, for example, that for loggers fitted to place about 30% will be recovered. For some fish, of course, the recovery rate will be considerably less.

The means of attachment of the logger to a fish will depend on the type of fish. For flat fish, such as place, attachment might be by means of a steel pin, the logger being attached to the unfinned side of the body. Other fish, such as salmon, can have the logger attached by means of sutures, a convenient site being adjacent to the dorsal fin. The logger will usually be of a domed, for example hemispherical shape.

Examples of typical sensors to be included in the logger are temperature and pressure, light level, sensors for measuring speed, direction of movement, compass heading or current flow speeds and directions, inclinometer, conductivity cell, heart-beat monitor, earth's magnetic field sensor, accelerometers and a tilt angle indicator.

Programming of the sensors will usually be such that some sensors will take readings at regular intervals whilst others will be used with greater regularity at particular seasons such as when the fish are known to breed or to migrate.

BRIEF DESCRIPTION OF THE DRAWINGS

Some embodiments of the invention will now be described, by way of example only, with reference to the accompanying diagrammatic drawings, of which:

FIGS. 7A and 7B are memory maps of the data logger.

DETAILED DISCUSSION OF PREFERRED EMBODIMENTS

Figure 1:
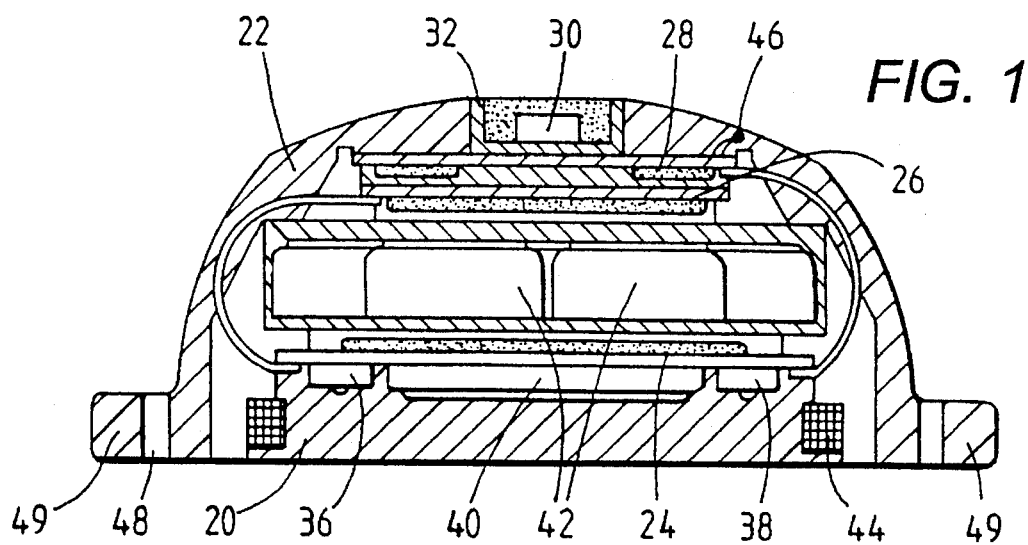
FIG. 1 is an elevation, in section along line I—I of FIG. 2, of a logger according to the invention.
Figure 2:
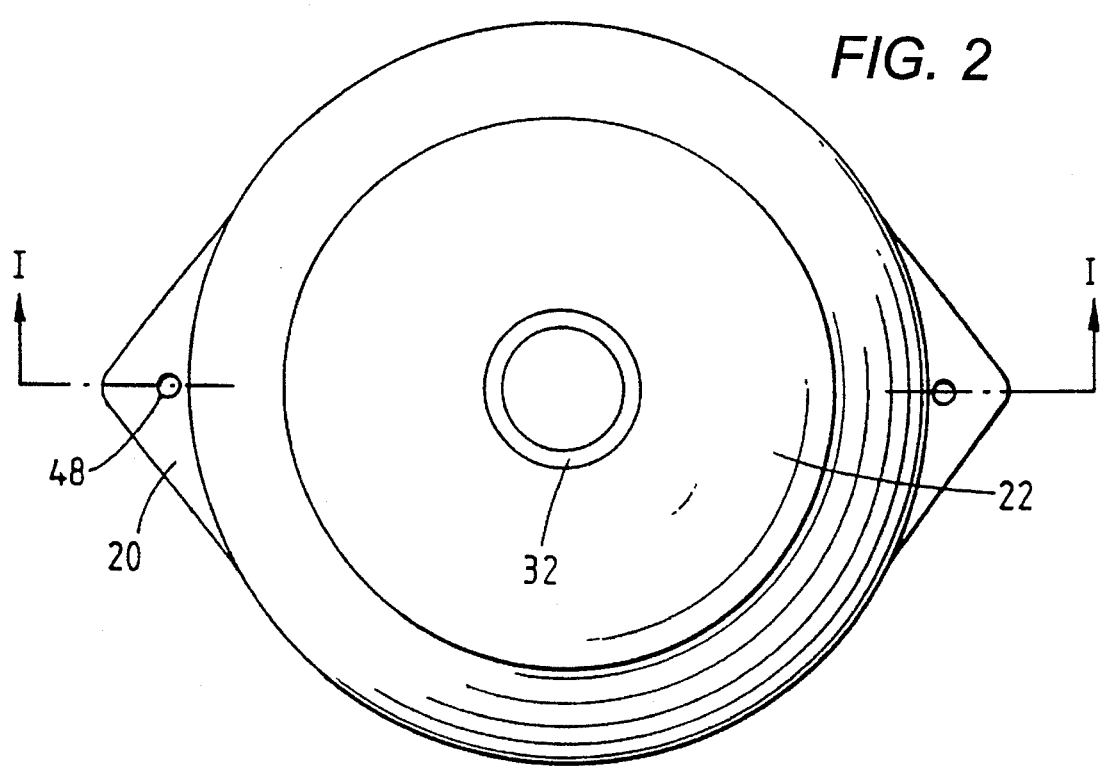
FIG. 2 is a plan view of the logger.

A typical data logger according to the invention (FIGS. 1 and 2), suitable for attachment to a fish, has a housing comprising a base of epoxy resin (of a type transparent to infrared radiation) which has an hemispherical dome 22 moulded thereto. Typical dimensions are a radius of 23 mm and a dome height of 22.6 mm. Enclosed within the base and dome are:

logger circuitry which includes a microcontroller-based programmable controller 24, a mass data store memory 26 and an analogue sensor board 28;

one or more sensors of which two are shown, namely a pressure sensor 30 and a temperature sensor 46;

power supplies, including main cells 42 and a standby cell 40;

a power up coil 44; and a detector 36 and a transmitter 38 by means of which the logger circuitry can be connected, without breach of the housing, to external circuitry to respectively transfer information to and from the logger circuitry.

Flanges 49, one at each end of a diagonal of the base 20, each have an eye hole 48 therein.

A suitable pressure sensor 30 might be, for example, a 0 to 150 psia chip coated with a water proofing material, mounted in a steel pot 32 which is filled with a gel providing mechanical protection. A typical sensor of this type is a Keller 3 Mi pressure sensor. A temperature sensor 46 might be, for example, a −5° C. to +25° C. Fenwall 192-103 LET-AOI thermistor bead. The main cells 42 might comprise seven Renata RE675 mercury cells, which provide a maximum of 9.8 volts and a typical end point voltage down to 5.5 volts, and the standby cell 40 might be a lithium cell. A suitable power-up coil 44 has 150 turns of 0.15 mm diameter enamelled wire, having a DC resistance of 16.6 ohms. A Honeywell infrared detector model SDP 8600-3 is a suitable detector 36 and a Honeywell infrared transmitter model SEP 8506-3 is a suitable transmitter 38.

The controller 24 might include a microcontroller, such as a Philips S87C552 which has built in a ten-bit analogue-to-digital converter, serial communication ports, parallel data ports and an erasable/programmable read-only memory (EPROM) for storing the microcomputer software, logic circuitry for switching between operating modes, supply management circuitry and a one minute sampling clock.

Figure 3:
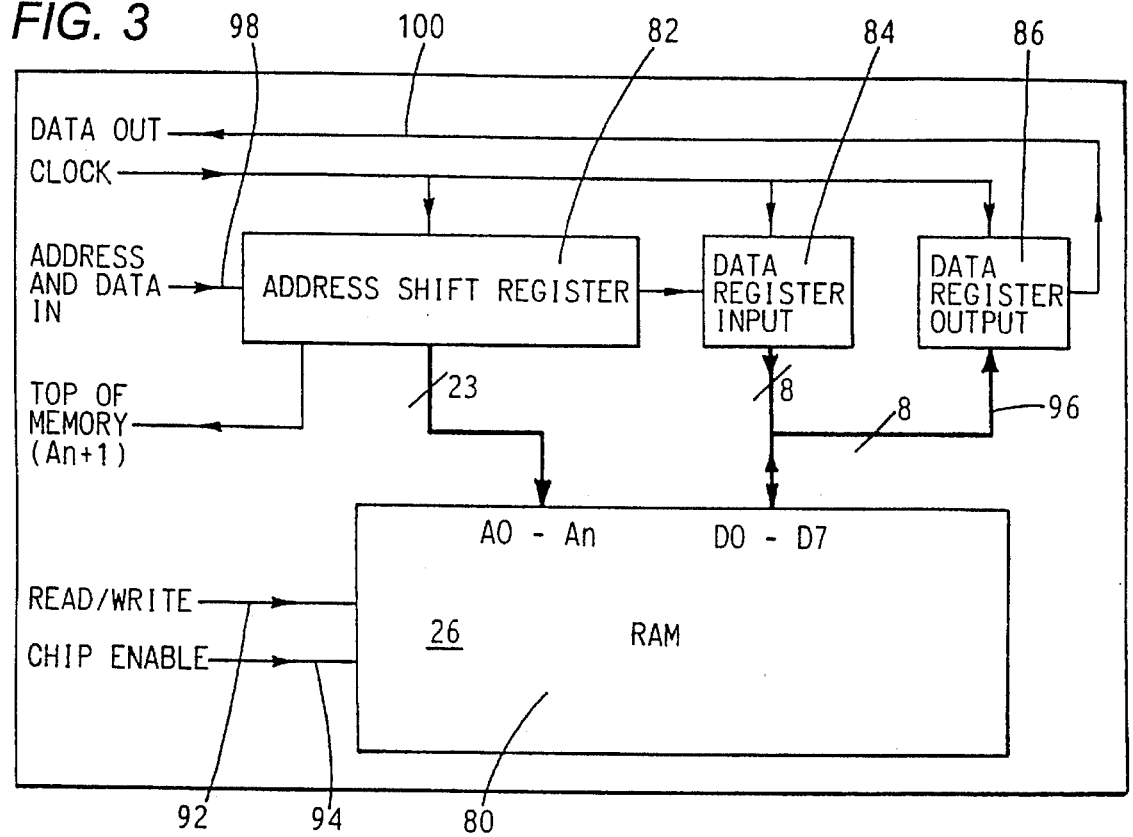
FIG. 3 is a block diagram of a data store.

A suitable memory 26 (FIG. 3) includes a Random Access Memory (RAM) 80, having a memory which, in practice, might be of the order of 8M byte, in conjunction with an address shift register 82, a data register input 84, and a data register output 86. The RAM has an input 88 from the address shift register 82, an input 90 from the data register input 84, a read/write input 92 and a chip enable input 94, and an output 96 to the data register output 86. The registers 82, 84 and 86 receive inputs from the clock in the controller 24 and the address shift register 82 has an address and data in input 98. The data register output 86 has a data out output 100.

Figure 4:
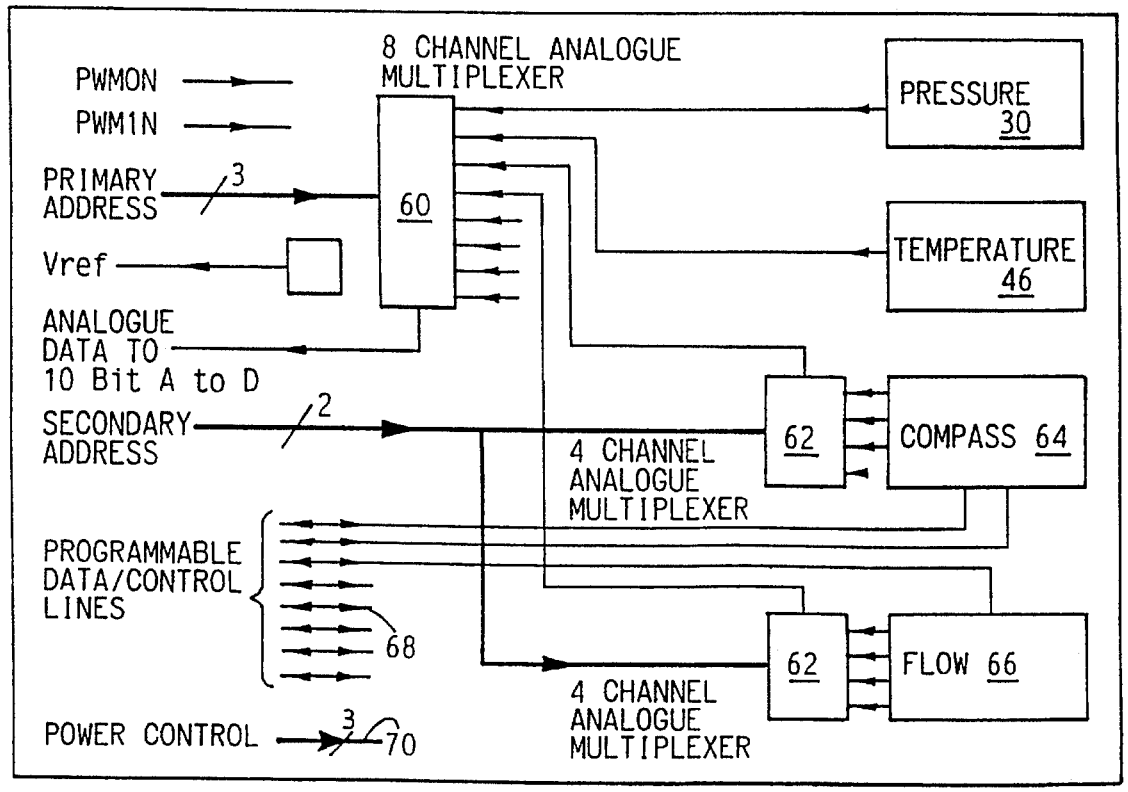
FIG. 4 is a block diagram of an analogue sensor circuit.

A typical analogue sensor board 28 (FIG. 4), accommodating a wide variety of proposed sensors with different drive conditions whilst offering the required flexibility uses a fixed interface. This enables boards with different sensor arrangements to be installed with no alterations to the logger. The primary analogue interface is an 8-to-1 multiplexer 60 controlled by three address lines each associated with a sensor channel. In FIG. 4 the pressure sensor 30 and temperature sensor 46 are illustrated connected to the 8-channel multiplexer 60. To accommodate sensors such as a compass 64 and a flow sensor 66, which have more than a single analogue output, a second 4 to 1 multiplexer 62 is used with two secondary address lines. Programmable data lines 68 enable the controller 24 to control sensor hardware and to read data from digital sensors such as a conductivity cell (not shown). Power control lines 70 enable high current sensors to be switched on under logger control only when they are needed, hence saving on cell power.

A logger with components as described above might conveniently be assembled with the power-up coil 44, detector 36 and transmitter 38 encapsulated in the resin of the base 20 as close as practical to the outer surface of the base allow optimum communication with equipment external to the logger. A stack of components might then be, in order outwardly from the base, the standby cell 40, controller 24, main cells 42, memory 26, and sensor board 28. This leaves the sensor board adjacent to those sensors such as the pressure sensor 30 and temperature sensor 46 which must of necessity be exposed to conditions external to the housing. The pressure sensor 30 is positioned at the top of the dome 22 and sealed from the rest of the housing and the temperature sensor 46 is positioned near the outer surface of the dome 22, both being connected to the sensor board 28. The circuit components 24, 26 and 28 are conveniently implemented in microelectronics on ceramic substrates.

The EPROM is programmed in accordance with the other contents of the logger prior to installation in the housing. Typical contents might include operating programs communication programs, test procedures and sensor drivers for each of the sensors within the housing.

Figures 5, 6:
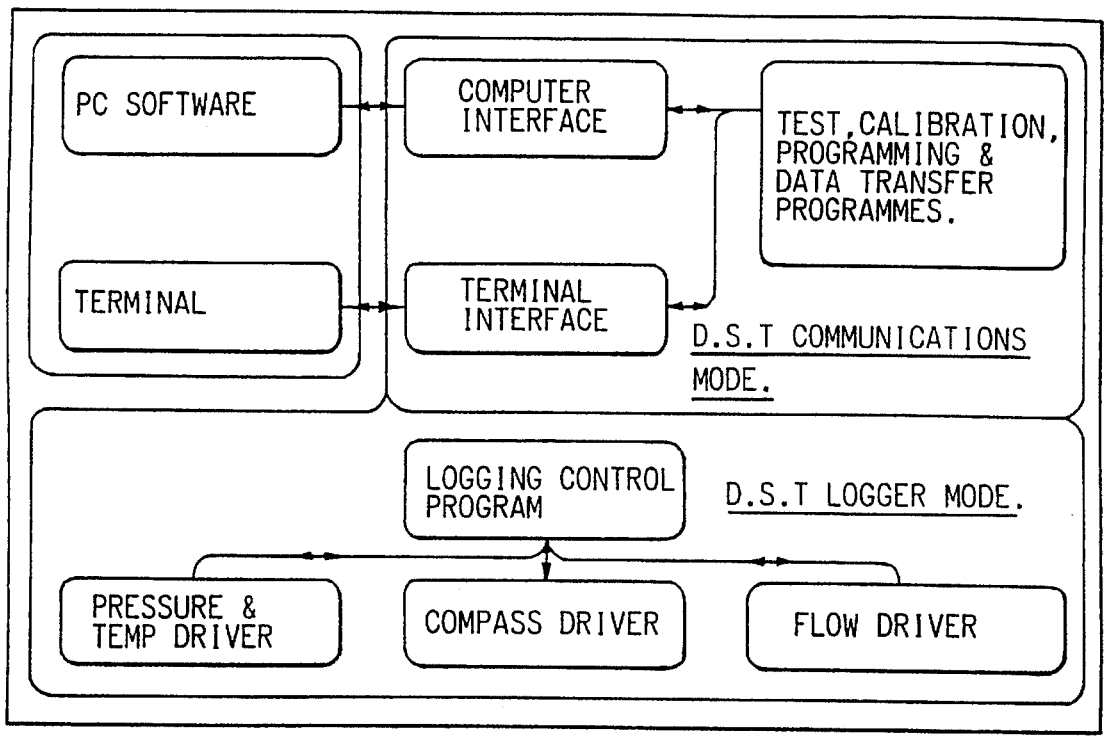
FIG. 5 is a software functional block diagram.
FIG. 6 is a table of sample instructions for the logger.

The logger operates in two modes, as illustrated in FIG. 5, switched by the logic circuitry in the controller 24. In the operational mode the logger is operating independently under control from the controller 24 and powered by the cells 42 or 44. In the communications mode the logger is driven by an external computer and power source.

For use, the logger is programmed, in the communications mode, according to the requirements of the mission for which it is to be used, which might, for example, require only some of the available sensors to be used. The logger is placed in an interface unit (not shown) which aligns the coil 44 with a magnetic field such that power to run the logger is induced in the coil. The coil thus provides power for running the controller 24, the infrared detector 36 and the transmitter 38 enabling bi-directional communications without having to make electrical contact which would otherwise require breaking the integrity of the sealed housing.

The logger is prepared for use by inducing a current in the power-up coil 44 and optically coupling the detector 36 and transmitter 38 respectively to a transmitter and a receiver in the interface unit, which are connected to an external computer (not shown). The logic circuitry in the controller 24 switches the logger to the communications mode, and the logger is set up by the external computer with purpose-designed software which uses pull-down menus and on-screen help, thus making all control functions, test functions, and programming etc, via on screen forms, friendly and intuitive. The manner in which the basic operating program is executed has to be varied to set the start, frequency and finish of each operating routine. FIG. 6 is an example of an on-screen form accessed from the menu which is edited by the user for setting the number and time interval between samples for each available sensor. In the embodiment shown there are eight sensor channels each having six sample sets, and each set being capable of 65,535 samples. Each channel is executed independently and each set can be separately programmed for a time interval between readings and number of samples. The sample taking is triggered by the one minute time clock in the controller 24. At each minute the controller 24 enables the passage of data derived from the sensors, provided the sample table time interval in minutes from the last sample has elapsed. Each channel set can also be programmed with a pause if zero is entered for the number of samples. The pressure sensor programme indicated in FIG. 6 (channel 2) will wait ten days, (14400 minutes) before taking 100 samples at hourly intervals, then 65,000 samples will be taken at three hourly intervals.

The user entered data is validated by the external computer, then organised in a format that can be stored and/or transmitted by the external computer to the logger. Other menus (FIGS. 7A and 7B) provide for the input of header information (e.g. date and time of deployment, identification information for use on the retrieval of the logger, and user comments), the control of test functions, the display of logger status information, the inputting and retrieval of calibration data, the retrieval and filing of logged sensor data, and the editing of the sensor table detailing the types of sensor or sensors installed in particular channels. FIGS. 7A and 7B illustrate the programmes stored in the EPROM as basic fop a particular logger and those loaded in the RAM 80 as part of the external programming.

The controller programme is preferably adapted to execute tests and calibration procedures on the sensors to check that the logger is functioning correctly whilst it is still being run externally through the interface.

On removal from the interface, or prior to attachment to a fish (for example by using a special subsidiary interface), the logger is activated by switching operation to the main batteries. The logger is then attached to a fish by means of pins passing through the eye holes 48, and the fish is then released into an appropriate environment. The operating program operates the sensors and the readings from the sensors are stored in the RAM 80 of the mass data store 26. Clearly the power available and the storage capacity of the mass data store are limited and the program will normally run for a predetermined period (for example one year) after which readings will cease and the system will switch to a storage mode using the standby cell 40. The controller 24 may also be programmed to detect loss of power, or low power, in the main cells 42, or exhaustion of data storage space and to switch to the storage mode on detection of any of these conditions. The standby cell is arranged to have sufficient power to retain the information in the memory 26 for a period of five years, after which the fish might reasonably be expected to have either been caught or to have died.

Once a logger has been recovered the information thereon is collected by a reverse of the programming process. The logger is connected to an interface as before, the coil 44 is powered, and the circuitry activated from the external computer to pass the information stored in the memory 26 through the infrared transmitter 38 whence it can be displayed on a screen, transferred to the computer for processing, or both.

A fuller explanation of some preferred or alternative details of the logger operation will now be given.

The operating instructions may be such that the instruction to each set will be executed in turn for each of the channels. Once the collection of samples for all sets for a particular sensor channel have been completed, that channel stops logging. When all the channels being used have completed the sample instructions for all the sets, the routine is complete and the logger takes no further samples, but is switched to the storage mode using the standby cell 40.

The three limitations on the number of samples that may be taken are: the size of the memory 26, the power cell 42 capacity and the maximum number of samples that can be set in the sample table. The maximum number of samples per sensor channel is typically approximately $4 \times 10^5$, and each channel may accommodate up to 4 data items per sensor. This results in a required memory size of 24M bytes for the whole table if all channels are to be used to their maximum. This is unlikely, and a more practical maximum memory capacity of 8M bytes is used. It is not practical to install this amount of memory in a logger without the cell capacity to utilise it fully (such as may be the case in some fish loggers) but with loggers for some other purposes, such as for animals where relaxed size restraints allow larger capacity cells 42 the full 8M bytes of memory can be used.

The mass data store memory 26 preferably has a serial interface to minimize the number of interconnecting wires and to enable various sizes of memory board (up to a maximum of, for example 8M bytes) to be connected to the logger. The logger uses the most significant address line plus one extra to detect the size of memory installed.

The logger software is arranged around the main internal operating program stored in the EPROM. The operation and sensor sampling is controlled by the instructions in the sample table. The internal operating program does not control the sensors directly, but uses the sensor table to command an appropriate sensor driver sub-program, stored in the EPROM, to operate the required sensor. This enables different sensors to be installed in any channel, and also makes it easy and quick to install new sensors. Installing a new sensor simply involves designing the hardware using spare control lines and writing a sensor driver programme (or taking one from a library of driver programmes) and installing it in the EPROM, then editing and loading the sensor table as normal via the external computer. This makes the internal operating program independent of the sensor complement and arrangement, and enables the EPROM to be programmed regardless of which sensor board is fitted.

Only one internal operating program and its associated set of drivers are required, and not a different program for each sensor complement and arrangement. When a sensor board is connected the sensor table is edited via the external computer to inform the internal operating program which sensor driver to use in which channel, and the control program in the EPROM is not affected. This reduces the chance of total failure since only a small, simple sub-program has to be written for each new sensor, and not the writing or editing of a larger more complex logger control program for every sensor arrangement and complement. This has the additional benefit that an error in the driver software, provided the driver returns control to the main operating program each time it is accessed, will only result in the loss of data in the associated channel.

The logger can be switched by the external computer via the interface unit to enter either an enabled or a disabled state. In the enabled state, when the logger is removed from the interface unit, the logger will, after a delay of one minute, start executing the sample table instructions. If the logger is switched to the disabled state, it can be programmed in advance of use with a sample table and comments etc, and when removed from the interface unit the logger will not execute the sample table, but will go into the storage mode and simply retain the information. The logger can be subsequently enabled and removed from the interface unit to start execution of the sample table, or the existing sample table or data modified. The power to retain the data when the logger is inactive is supplied by the standby cell, and supplied by the main cells only when the logger is enabled.

Figure 8:
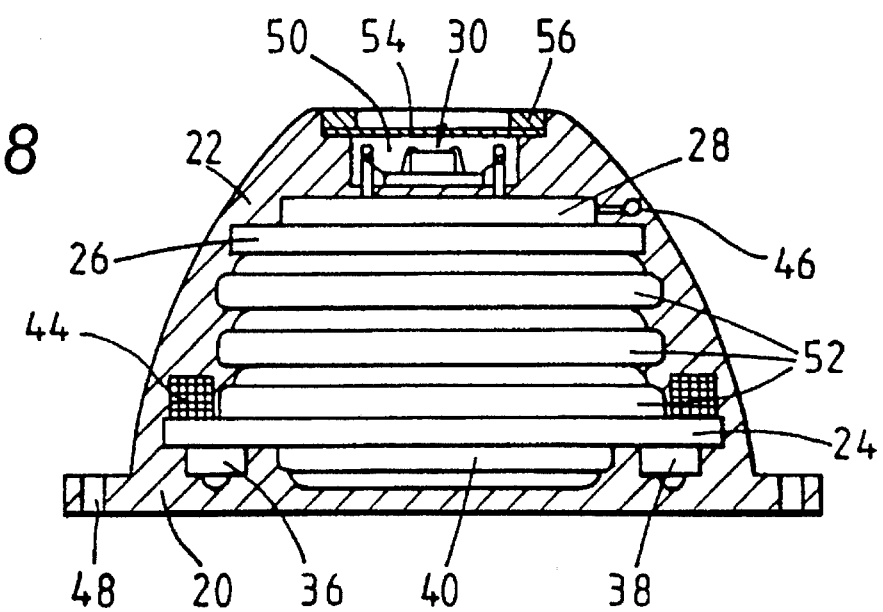
FIG. 8 is an elevation, in section along line II—II of FIG. 9, of another embodiment of the invention.
Figure 9:
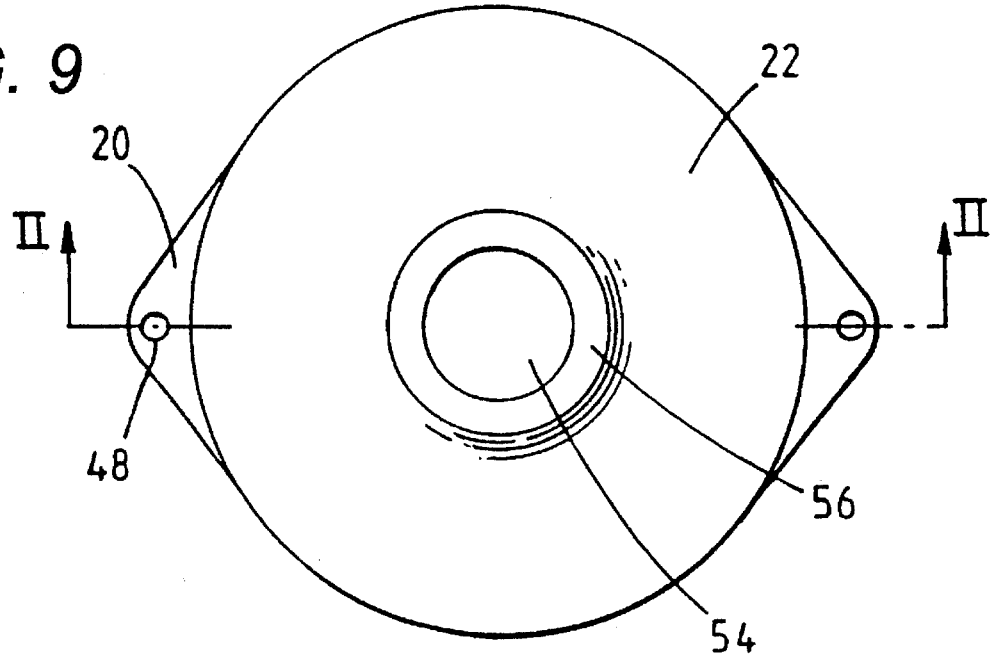
FIG. 9 is a plan view of the logger of FIG. 8.
Figure 10:
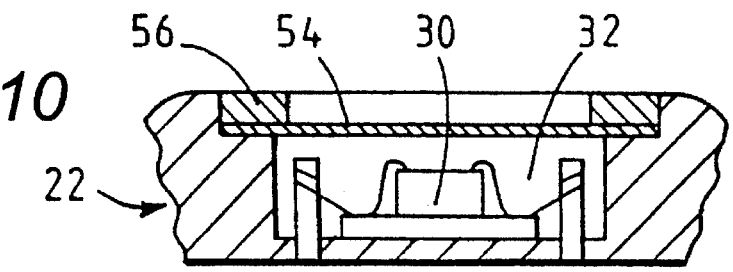
FIG. 10 is an elevation, in section along line II—II of FIG. 9, of a detail of the logger.
Figure 11:
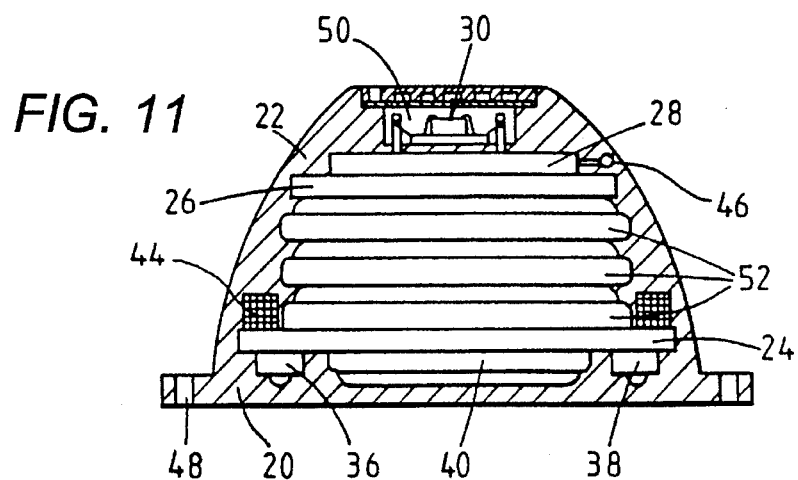
FIG. 11 is an elevation, in section along line III—III of FIG. 12, of another embodiment of the invention.
Figure 12:
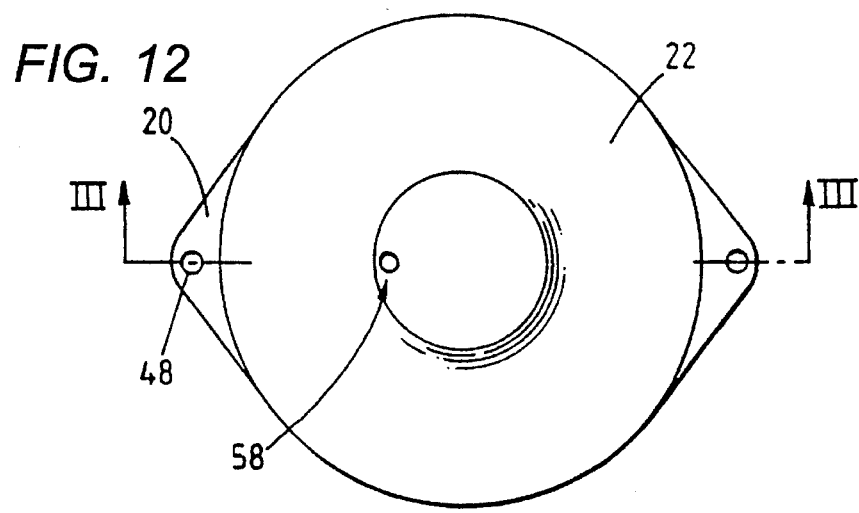
FIG. 12 is a plan view of the logger of FIG. 11.
Figure 13:
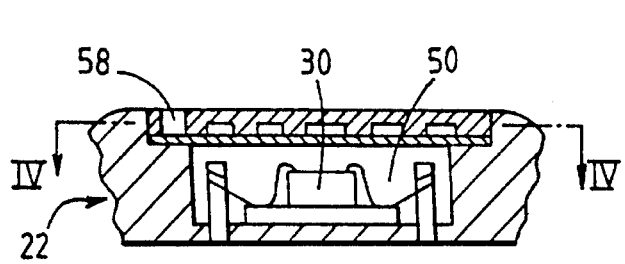
FIG. 13 is an elevation, in section along line III—III of FIG. 12, of a detail of the logger.
Figure 14:
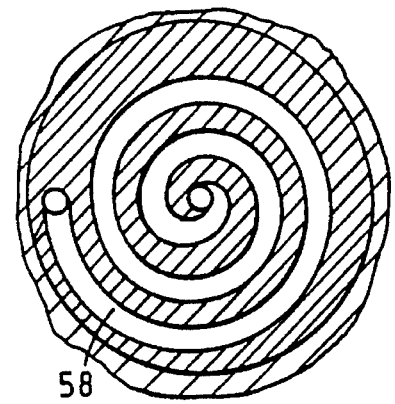
FIG. 14 is a plan view, in section along line IV—IV of FIG. 13, of part of the detail in FIG. 11.

In another version of the invention, (see FIGS. 8 to 14), in which like numbering is used, the arrangement of the items is somewhat different. An alternative form of pressure capsule has e recess 32 (FIGS. 8 to 10) filled with silicon fluid sealed in by a pressure responsive diaphragm 54 held in place by a polycarbonate clamp ring 56 or by cap 58 (FIGS. 11 to 14) in which is a spiral capillary connecting fluid within the recess to the environment. Wit the capillary arrangement there will be some seepage of fluid from the recess but with suitable design of the capillary the arrangement will survive the expected life of the logger.

It will also be realised that depending on the application of the logger, many other cell types and capacities can be used.

The selection of sensors will depend on the information required are the availability of suitable sensors to fit within the logger housing. Sensors are positioned as appropriate within the housing. A temperature sensor might, for example, be sited on a surface of the analogue sensor board 28 where, although insulated from the environment, the rate of change of temperature might be expected to be so low as to make this insulation of little consequence. Alternatively, a temperature sensor could be encapsulated in the epoxy of the housing nearer its outside surface. It will be realised that the sensitivity of various components of the logger and the harshness of the environment in which it is expected to operate require the sealing of the dome 22 to be very thorough. The suggested arrangement allows the logger to be programmed and interrogated without the integrity of the housing being breached.

Whilst the version described uses a receiver and transmitter operating in the infrared waveband for transferring data other arrangements may be used without breaching the housing. For example radio, magnetic coils, capacitor plates or other forms of data transmission will be readily apparent to those skilled in the aft.

It will also be realised that loggers according to the invention have many potential uses other than with fish. Some of the many alternative uses are the tagging of farm or wild animals, labelling of cargo and factory produced goods for transport, administration of 5 legislation referring to vehicular, marine and air transport, and in medicine.

Apart from the individual programming of sensors mentioned above (for example the programs for the temperature sensor 42 and pressure sensor 30 described with reference to FIG. 6) the present invention allows for sensors to be brought into use on a contingency basis. By this is meant that if readings from the sensors in use indicate conditions where readings from a sensor not in use would be of value that sensor might be brought into use by the controller 24.

What is claimed is:

1. A data logger including a housing containing at least one sensor;

programmable control means;

a Random Access Memory (RAM) providing data storage means for storing data from the at least one sensor;

power means;

electro-magnetic transfer means for accessing the logger and for recovering data from the data storage means from external to the housing, wherein the programmable control means includes a pre-programmed Erasable Programmable Read Only Memory (EPROM) containing control instructions including an operating program, and a sensor driver for each of said at least one sensor;

the RAM is adapted to accept, from external to the housing and via the electro-magnetic transfer means, a sensor table accessible by the operating program for commanding the appropriate sensor driver to operate the required sensor and a sample table accessible by the operating program containing instructions on the operation of each sensor to evoke a desired sampling regime; and a power up coil is provided within the housing to enable power from external to the housing to be supplied during programming and during recovery of data.

2. A data logger as claimed in claim 1 characterised in that the instructions in the EPROM include a communications program.

3. A data logger as claimed in claim 1 characterised in that the control instructions in the EPROM include a test procedure program.

4. A data logger as claimed in claim 1 characterised in that the housing (20, 22) is waterproof.

5. A data logger as claimed in claim 1 characterised in that the power means are in the form of electric cells (42).

6. A data logger as claimed in claim 1 characterised in that logger is designed to protect stored data by switching to a disabled state automatically once it has completed a sample table, when the mass data store is full, or when it detects that the power supply is low.

7. A data logger as claimed in claim 1 characterised in that the logger includes a standby cell (40) for operation in the disabled state.

8. A data logger as claimed in claim 1 characterised in that it is suitable for attachment to a fish.

9. A data logger as claimed in claim 1 characterised in that the electro-magnetic transfer means use light.

10. A data logger as claimed in claim 9 characterised in that the light is infrared.

11. A data logger as claimed in claim 1 characterised in that it includes a plurality of sensors including sensors selected from a group for measuring temperature, pressure, light level, speed, direction of movement, compass heading, current flow speed, current flow direction, inclination, conductivity, heart-beat, earth's magnetic field, acceleration and tilt angle.

12. A data logger as claimed in claim 11 characterised in that it is programmed for operation of a selection of sensors, at least one of the sensors being individually programmed.

* * * * *